(12) United States Patent
Powder et al.

(10) Patent No.: US 9,611,105 B1
(45) Date of Patent: Apr. 4, 2017

(54) PNEUMATIC TUBE DELIVERY SYSTEM HAVING TRANSPORT CHARACTERISTICS RESPONSIVE TO PAYLOAD ITEM-ACQUIRED

(71) Applicant: Pevco Systems International Inc., Baltimore, MD (US)

(72) Inventors: William Cooke Powder, Baltimore, MD (US); Steven Dahl, Baltimore, MD (US)

(73) Assignee: PEVCO SYSTEMS INTERNATIONAL INC., Baltimore, MD (US)

( * ) Notice: Subject to any disclaimer, the term of this patent is extended or adjusted under 35 U.S.C. 154(b) by 234 days.

(21) Appl. No.: 14/212,403

(22) Filed: Mar. 14, 2014

Related U.S. Application Data

(60) Provisional application No. 61/788,869, filed on Mar. 15, 2013.

(51) Int. Cl.
*G06F 7/00* (2006.01)
*B65G 51/42* (2006.01)

(52) U.S. Cl.
CPC ................................ *B65G 51/42* (2013.01)

(58) Field of Classification Search
None
See application file for complete search history.

(56) References Cited

U.S. PATENT DOCUMENTS

| | | | |
|---|---|---|---|
| 7,243,002 B1 * | 7/2007 | Hoganson | B65G 51/44 406/4 |
| 2014/0081448 A1 * | 3/2014 | Hoganson | B65G 51/36 700/230 |
| 2014/0305227 A1 * | 10/2014 | Johns | B01D 21/262 73/863.01 |

* cited by examiner

*Primary Examiner* — Yolanda Cumbess
(74) *Attorney, Agent, or Firm* — Fay Kaplun & Marcin, LLP

(57) ABSTRACT

A method for transporting items via a delivery system includes identifying an item to be transported via the delivery system by acquiring identifying information from an identifying element applied to the item, determining an item-specific transport characteristic of the item based on the acquired identifying information and setting parameters for a transport of the item based on the transport characteristic of the item.

23 Claims, 3 Drawing Sheets

PNEUMATIC TUBE DELIVERY SYSTEM HAVING TRANSPORT CHARACTERISTICS RESPONSIVE TO PAYLOAD ITEM-ACQUIRED

PRIORITY CLAIM

The present application claims priority to U.S. Provisional Application Ser. No. 61/788,869 filed on Mar. 15, 2013 entitled "Pneumatic Tube Delivery System Having Transport Characteristics Adaptively Determined Responsive to Payload Item-Acquired Information," the entire disclosure of which is incorporated herein by reference.

FIELD OF THE INVENTION

The present invention is generally directed to a pneumatic tube delivery system having transport characteristics such as transaction priorities, delivery constraints, requisite collateral actions, or the like adaptively determined responsive to various information acquired for or from a payload item to be transported. More specifically, the subject system safely, securely, and timely transports various items in carrier apparatuses through the tubular conduits of a pneumatic tube delivery system maintaining intelligent management and control over delivery adaptively suited to transported items.

BACKGROUND

Pneumatic tube delivery systems are widely used in various institutions implemented in different forms depending on the nature of the operations and transactions carried out at a particular facility. Nonetheless, the systems generally share certain basic components. First, a network of tubular conduits is established throughout the facility, branching to user outlets connected to respective send/receive workstations, or portals. Items of interest may be transported between user outlets via the delivery tubes in capsule-like carriers, the contents of which are filled, for example, by users at originating outlets and emptied by users at a receiving outlets. Alternatively, a packaging of the item itself may act as the carrier so that the item is not required to be housed within a separate carrier apparatus for delivery. The carrier's travel through the network of tubular conduits is driven by one or more blower units which generate pneumatic flow (such as by vacuum pressure) sufficient to propel the capsules through different portions of the network. Typically, a computer-based controller unit(s) operates to regulate carrier traffic and maintain overall system operation.

The network of tubular conduits may be quite complex even in modest sized facilities, since delivery access between every combination of user outlets is often required. The network generally incorporates multi-port diverters, or transfer units, at intermediate points physically transferring carriers from one branch (or section) of the tubular conduit network to another for delivery to the proper destination outlet. While such diverter/transfer units markedly reduce redundancy in conduit segments, the network remains quite elaborate in systems serving numerous outlets, with individual conduit segments making numerous turns and bends to serve the many user outlets.

Pneumatic tube delivery systems are employed, for example, in financial institutions such as banks to remotely conduct customer transactions in real time. Industrial and retail facilities also employ these systems to transport payload items such as documents, currency, parts, or merchandise from one location to another. Perhaps the most prevalent and demanding uses may be in healthcare institutions such as hospitals, where the need for quick, efficient and secure physical transport of items between remote locations within the facility tends to be the rule, not the exception. Items such as pharmaceuticals, lab specimens, blood products, and the like must be passed between different staff members quickly and reliably. It is not uncommon for a hospital to carry out several thousands of transports of delicate payloads like this on a daily basis.

In healthcare settings, for instance, certain items like blood work and other test results, may be highly time sensitive. They may be of greater urgency than other deliveries that entered the delivery 'queue' earlier and are awaiting traffic control clearance for delivery initiation. Also, there may be certain handling protocols and restrictions that must be followed for certain types of payload items, as determined by a given institution's business or field of endeavor.

Hence, there is a need for a system which adaptively prescribes and carries out transport characteristics appropriate for specific payload items based on information the system acquires for or from the items.

SUMMARY OF THE INVENTION

The present invention is directed to a method for transporting items via a delivery system. The method includes identifying an item to be transported via the delivery system by acquiring identifying information from an identifying element applied to the item, determining an item-specific transport characteristic of the item based on the acquired identifying information, and setting parameters for a transport of the item based on the transport characteristic of the item.

The present invention is also directed to a system for transporting items. The system includes an identifying element affixed to an item to be transported between stations of a network of delivery conduits, the identifying element including identifying information regarding the item, an identification reader acquiring the identifying information from the identifying element, and a processor analyzing the identifying information to determine an item-specific transport characteristic of the item based on the acquired identifying information and setting parameters for a transport of the item based on the transport characteristic of the item.

In another aspect, the present invention is directed to a pneumatic delivery system. The pneumatic delivery system includes a network of delivery conduits extending between a plurality of sending stations and receiving stations, an identifying element affixed to an item to be transported between one of the sending stations and one of the receiving stations, the identifying element including identifying information regarding the item, an identification reader acquiring the identifying information from the identifying element, and a processor analyzing the identifying information to determine an item-specific transport characteristic of the item based on the acquired identifying information and setting parameters for a transport of the item based on the transport characteristic of the item.

The present invention is also directed to a non-transitory computer readable storage medium including a set of instructions executable by a processor, the set of instructions, when executed by the processor, causing the processor to perform operations, including identifying an item to be transported via the delivery system by acquiring identifying information from an identifying element applied to the item, determining an item-specific transport characteristic of the item based on the acquired identifying information, and setting parameters for a transport of the item based on the transport characteristic of the item.

DETAILED DESCRIPTION

Figure 1:
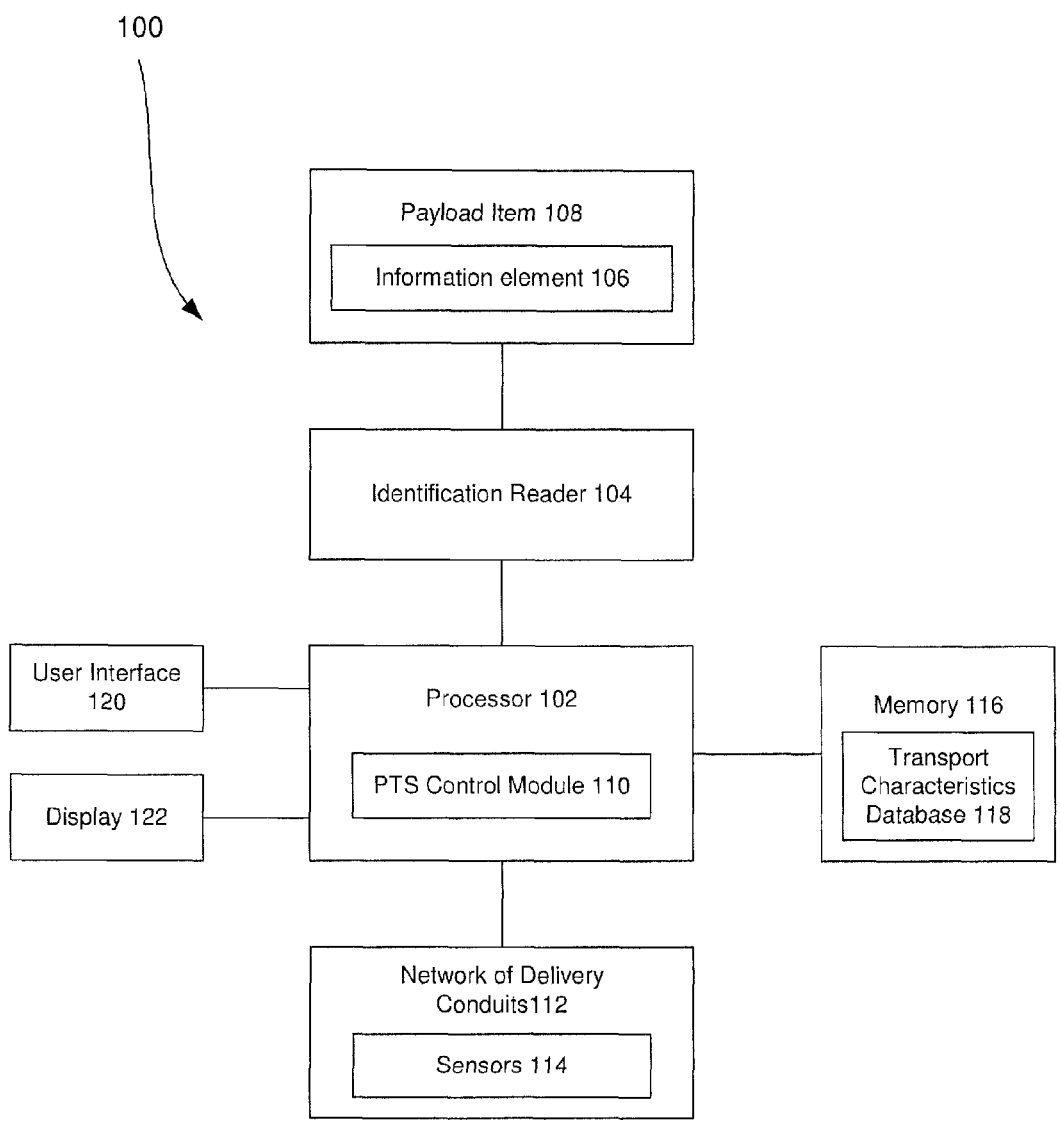
FIG. 1 shows a schematic diagram of a pneumatic tube delivery system according to an exemplary embodiment of the present invention.

The present invention may be further understood with reference to the following description and the appended drawings, wherein like elements are referred to with the same reference numerals. Exemplary embodiments of the present invention describe a pneumatic tube delivery system and method for acquiring item-specific information pertaining to payload items to be transported through its pneumatically driven conduits between a sending station and a receiving station. The exemplary system and method include measures programmably configured to maintain intelligent control over transport management and operational interaction with other systems and infrastructures within a given host facility. Measures are preferably employed at or near each of the sending workstations by which the system acquires item-specific information for different transport payloads from various information bearing parts of the item. For example, a barcode, tag, or label-carried indicia may be read from the item. Information may be read from an electronic transponder, RF identification tag, or the like. Alternatively, photographic images or any other form of item-specific data may be captured using one or more suitable sensing means known in the art. Although the exemplary embodiments of the present invention specifically describe the transport of items via a pneumatic tube delivery system, it will be understood by those of skill in the art that the system and method of the present invention may be used in any of a variety of transport/delivery infrastructures in which acquiring item-specific information for the payload item to be transported would be desirable.

Based on the payload item(s) information of interest acquired, the system adaptively establishes applicable transport characteristics pertaining to the given transport for this particular payload. Such transport characteristics may include transaction priorities, delivery constraints, requisite collateral actions, or the like. The range, scope, nature, and/or type of those transport characteristics will vary with the institution or facility making use of the system, and its field of endeavor. They will depend on such things as the business or other operation rules/constraints according to which the institution operates; the particular make up of its staff, patients, customers, clients; the values that the institution holds to; any regulatory requirements the institution must comply with; various organizational protocols imposed on the institution; and various other factors along these lines which may bear on the particular facility in question.

Preferably, the type of information to be acquired from the payload items is determined according to the transport characteristics of interest. The system controller adaptively sets the appropriate transport characteristics for each transport transaction in question responsive to the information specifically acquired from the transport's payload item(s). The transport transaction is then carried out according to the transport characteristic settings, via, for example, a carrier apparatus through the system. Thus, where the information acquired for a payload item indicates that it is highly time-sensitive, for instance, the priority of delivery is appropriately set and the transport transaction carried out as expeditiously as the priority level dictates. In addition, if the transaction characteristics include additional actions beyond priority level adjustment, those actions are concurrently or collaterally effected by the system as well. These actions may include, for instance, the dissemination of appropriate alerts to one or more parties and locations affected by the transport transaction. It will be understood by those of skill in the art that although the exemplary embodiments describe carriers and carrier apparatuses, the payload items are not required to be separately housed in a carrier apparatus and, in some situations, the packaging of the payload item itself, may act as the carrier.

Figure 2:
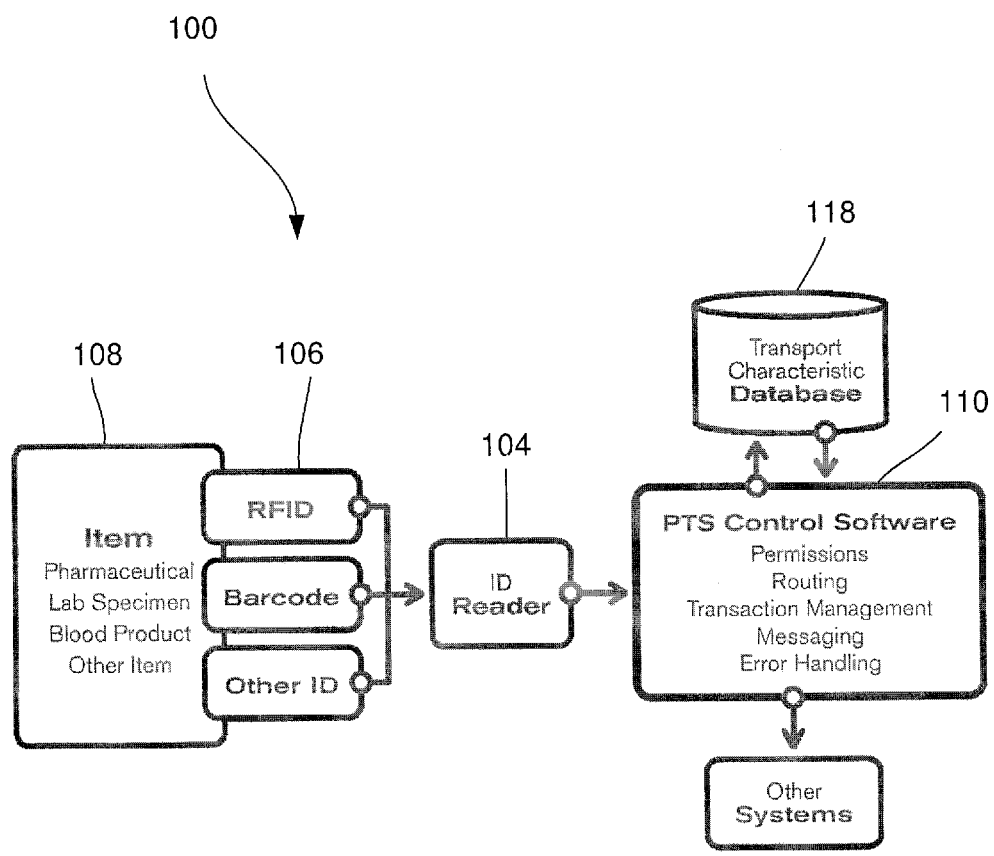
FIG. 2 shows another schematic diagram of the system of FIG. 1.

As shown in FIGS. 1 and 2, a pneumatic tube delivery system 100 according to an exemplary embodiment of the present invention comprises a processor 102 receiving information from an identification reader 104 which reads information from an identifying element 106 of a payload item 108 to be delivered/transported via a network of tubular conduits 112. The network of tubular conduits 112 may include a plurality of stations between which the items 108 may be transported, as desired. The conduits 112 may additionally include sensors 114 at a plurality of positions therewithin for tracking the positions of items within the network of conduits 112. The system 100 may further comprise a memory 116, a user interface 120 and/or a display 122. The memory 116 may store information related to the item(s) 108 and include a Transport Characteristics Database 118 including information regarding transport characteristics associated with particular items. The user interface 120, via which a user may input information to initiate a transaction or provide information for facilitating a transaction, may include input devices such as, for example, a keyboard, a mouse, and/or a touch screen on the display 122 or any other suitable input device. In one example, the user interface includes a touch screen or touch control with an integrated barcode reader as the identification reader 104. The display 122 may display information regarding the item 108 and/or the transaction.

The identifying element 106 in this exemplary embodiment includes an RFID tag (electromagnetically readable radio frequency identification transponder, circuit, tag, or the like), a barcode, QRC code, or any other suitable form of identification/indication known in the art, affixed to or included on/in a carrier of the payload item 108. The processor 102 includes a Pneumatic Tube Delivery System (PTS) control module 110 for determining transport characteristics and payload priorities of each of the payload items 108 to be delivered by the system 100. The information-bearing element 106 may include identifying information which may be mapped to transport characteristics associated with specific identifying elements. For example, where the item 108 is identified as a blood sample which requires testing to be conducted within a particular time frame, the item 108 may be mapped to a transport characteristic identifying the item 108 as a transport priority having a preferred route. Based on the identified transport characteristics, the PTS control module 110 may determine optimal routing and scheduling of the payload's transports, and order its delivery transactions accordingly (relative to other delivery transactions to also be carried out by the system 100).

Transport characteristics such as payload priorities are determined and suitably indicated in item-specific manner for all or certain ones of the delivery jobs to be carried out through a given pneumatic tube delivery system. The PTS control module 110 is equipped and configured to acquire a payload's priority in this manner through acquisition measures applied to such ID/indicia. The processor 102 then responsively determines the optimal routing and scheduling of the payload's transports, and orders its delivery transaction accordingly (relative to other delivery transactions also to be carried out by the system). The system 100 also orders other collateral actions to be carried out for the transaction, as determined by information contained in a database preferably custom configured for the given institution/organization/facility.

The payload items 108 to be transport through the system are often already applied at conspicuous portions thereof with one or more informational labels or other suitable indicia for unique identification. The identifying indicia may include for instance a barcode unique to a particular item or a particular user department, as well as indicating the nature and time urgency of the payload item(s) 108. In a hospital setting, for example, pharmaceutical items are usually barcoded according to one or more standard formats. For example, such indicia may be applied on outer surfaces of the pharmaceutical package. The particularities of the label or other identifying indicia will be as required for the intended application to enable unambiguous identification (or classification, or categorization) of the payload item 108 and acquisition of its priority- or other transaction characteristic-determining information pertaining thereto, when the item is being prepared to leave a workstation, or when it is being otherwise handled at a workstation prior to departure. In certain embodiments, the identification readers 104 for acquiring the payload item-specific information are situated and oriented in cooperation with carrier tracking equipment that may already be provided in the given pneumatic tube delivery system 100 for automated or semi-automated reading.

The identification element 106 may include, for example, a barcode or RFID tag, to provide item-specific transport and delivery characteristics. Pneumatic tube systems may, for example, transport pharmaceuticals, lab specimens and blood products throughout a hospital. Most items sent in pneumatic tube systems are barcoded—either by the item's manufacturer or by hospital staff. The system 100 integrates an identification reader 104 (e.g., barcode scanning) into its pneumatic tube system as a way to track and document transactions. In an exemplary embodiment, a first user tracks and documents a transaction by scanning a barcode on each item sent, as well as a barcode on the carrier. The same elements may then be scanned by a second user who receives the items and its carrier at the destination. The data from the barcode is combined with data obtained by sensors 114 throughout the tubular conduits 110 that monitor each carrier of the payload items 108 as it travels inside the system's steel tubing 110. This embodiment enables users to check the progress of the item 108 en route, confirm its arrival and review historical data for completed transactions.

With the integration of the Item-Specific Transport Characteristics disclosed herein, the system 100 includes the identification element 106 such as a barcode or any other form of identification such as RFID applied/attached to an item 108 transported by the pneumatic tube system 100 to determine how the item 108 is to be handled by the system 100. With this method, characteristics are assigned to an item and entered into a transport characteristic database 118 stored in a memory 116. The pneumatic tube system 100 learns the relevant characteristics by reading the identification element 106 on the item 108 and checking the database 118 containing the item's characteristics. The system 100 then executes the transaction along with whatever characteristics are assigned to the item 108 being transported. Transport characteristics may include, but are not limited to: transaction priority, preferred routing, staff alerts, alert or other action at origin and destination stations, alert other hospital systems, staff access permissions, location restrictions, time of day restrictions, control software graphical user interface messages, error handling preferences, and empty carrier handling.

Transaction Priority

An item 108 may be assigned a transaction priority from low to high. For example, an item 108 with a high priority, such as a blood product, will automatically move to the front of a transaction pending queue and leave its origin station as quickly as possible—ahead of transactions at other stations that may have waited longer. Once en route, an item 108 with high transaction priority may continue to receive preference for any needed device and pipe routes within the network 112.

Preferred Routing

An item 108 can be assigned to preferred routes within the network of conduits 112. For example, an item 108 with preferred route characteristics may have sole or preferred access to interzone pipes or other connections between hospital departments.

Staff Alerts

A request to deliver a specific item 108 may trigger alerts to specific employees or groups of employees. Alerts may take the form of email, text messages, electronic message boards or other electronic communications and may also integrate with other hospital systems such as nurse call systems. Alerts may, for example, be initiated when a send request is first made, upon an item's departure from a station, when an item arrives at a destination station or when an item's delivery is delayed.

Alert or Other Action at Origin and Destination Stations

A request to deliver a specific item 108 may trigger an alert or other action at the station originating the delivery and at the station receiving the delivery. Station alerts may include electronic visual alerts such text, graphic and video messages and audio alerts such as alarms, chimes and tones. Station alerts may appear on the station's display or on a separate monitor/display associated with a station or a group of stations. Other actions may include holding a carrier and its contents in a secure location above a station until a secondary action, such as a badge swipe from an authorized employee, releases the carrier.

Alert Other Hospital Systems

A request to deliver a specific item 108 may trigger a message to other hospital systems and databases such as inventory management, billing, security and human resources.

Staff Access Permissions

An item 108 may be assigned access permissions where certain employees are authorized to handle said item while others are prohibited. For example, certain employees and employee groups may be prohibited from receiving narcotics that have arrived at a pneumatic tube station.

Location Restrictions

An item 108 may be assigned characteristics that limit where it can and cannot be sent within the network 112 of the pneumatic tube system 100. For example, a blood product characteristic may indicate that it cannot be sent to a maintenance or admissions department station.

Time of Day Restrictions

An item 108 may also be assigned characteristics that indicate the times of day it can be sent in a pneumatic tube system. For example, a lab specimen characteristic may indicate that it cannot be sent to a specialty lab during hours when the lab is closed.

Control Software Graphical User Interface Messages

An item 108 may be assigned characteristics that trigger certain treatments by the Control Software's graphical user interface. For example, a blood product or other high value item may be represented on the GUI with a unique icon or color to indicate certain qualities of the item or the item itself.

Error Handling Preferences

An item may be assigned characteristics that indicate how the pneumatic tube system handles error conditions. For example, a low value item may be allowed to remain in an undelivered error state for a longer amount of time than a high value item. An item's characteristics may indicate that should an error occur, certain employees or other hospital systems be notified.

Empty Carrier Handling (e.g., when the Item 108 is the Carrier Itself)

A carrier or carriers may be assigned characteristics indicating how the carrier is to be managed by the tube system 100. Examples include how the system handles a carrier that is empty. When the carrier is scanned and a transaction request is created to return the carrier to the system as an empty carrier, the carrier's characteristics may dictate where the carrier may go, or where the carrier may not go.

It is noted that the exemplary embodiment of the system 100 has been described with reference to a hospital setting. However, those skilled in the art will understand that similar concerns regarding prioritizing different payloads will exist in a variety of businesses and may be implemented in a similar manner. The identification element 106 may include, for example, a barcode or RFID tag on an item 108 (such as a pharmaceutical) and can be used to identify the patient receiving the item 108. Information read from the identification element 106 along with information from a database that includes the location of the patient along with the address of the closest pneumatic tube station is used to determine an optimal route of the pharmaceutical item 108 through the network of conduits 112. The pneumatic tube delivery system 100 would then automatically address and send the item and its carrier to the appropriate station.

Figure 3:
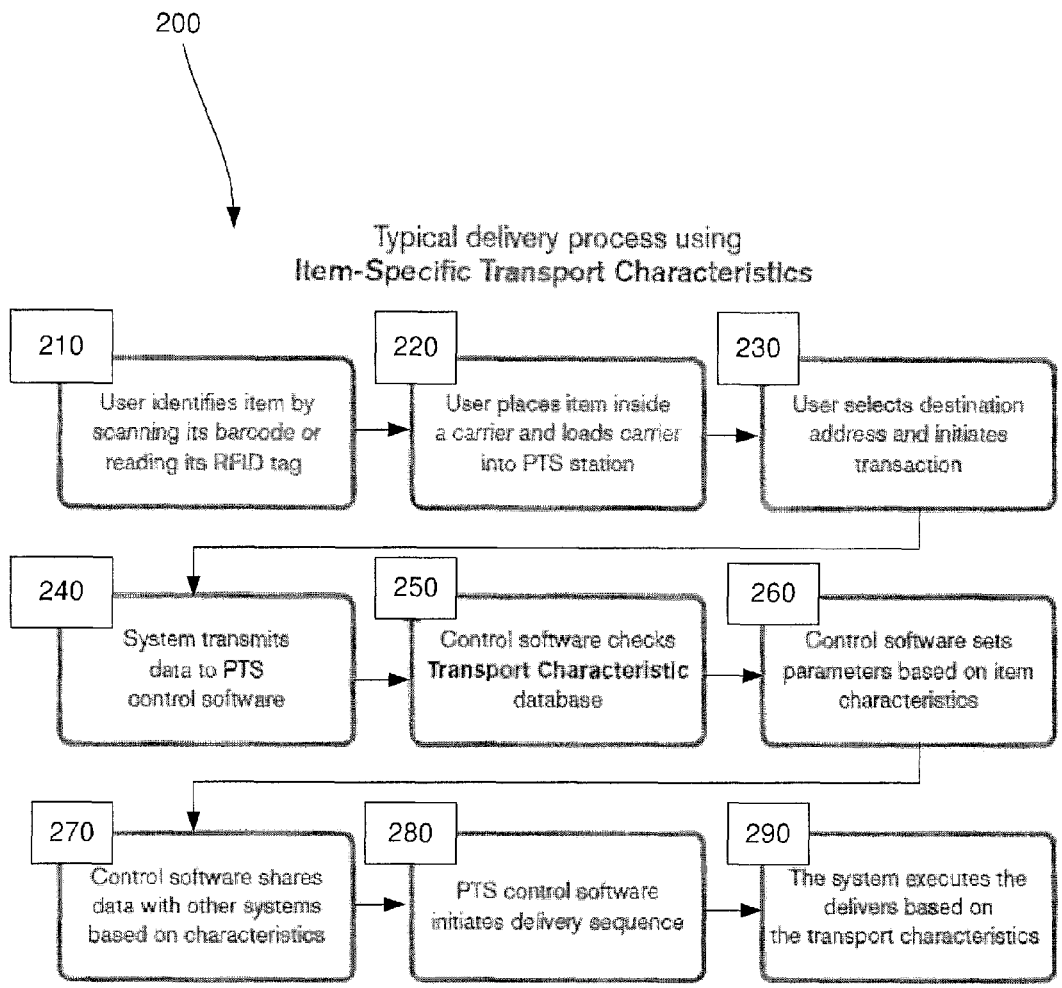
FIG. 3 shows a flow diagram of a method according to an exemplary embodiment of the present invention.

FIG. 3 shows an exemplary method 200 carried out by the system 100 implemented in accordance with an exemplary embodiment of the present invention. This exemplary flow of process is provided for illustrative general reference by the system 100 and operation features described herein.

Using the information reader 104, a user identifies the item 108 to be transported by reading the identifying element 106 thereof, in a step 210. The identifying element 106 may include transport characteristics data such as, for example, payload priorities. The item 108 may then be placed in a carrier, in a step 220, which is subsequently loaded into a sending station of the network of conduits 112. In a step 230, the user selects a destination address and initiates the transaction via the user interface 120. The system 100 then transmits the identifying information read from the identifying element 106 to the PTS control module 110, in a step 240. The PTS control module 110 'looks up' transport characteristic information of the identified item 108 from the Transport Characteristic Database 118, in a step 250, to determine characteristics that apply for that particular item 108. For example, the item 108 may be identified as having a transaction priority, preferred routing or may trigger an alert to varying parties within a facility. In a step 260, the PTS control module 110 will set parameters based on the item parameters identified in the step 250. For example, where a transaction priority has been identified, the PTS control module 110 will move the item 108 to the front of a queue of items to be sent out. In some situations, in a step 270, the PTS control module 110 may also share data with other systems/departments based on the identified characteristics. For example, where the system 100 is utilized within a hospital setting, one of the identified transport characteristics may indicate that an alert should be sent to a different department within the hospital such as, for example, inventory management, billing, security and/or human resources. Once all of the parameters for each of the identified transport characteristics have been set, the PTS control module 110 initiates a delivery sequence, in a step 280. The system 100 then executes the delivery/transport of the item 108 based on the identified transport characteristics and the set parameters.

The above described steps of the method 200 will be described in further detail below in regard to items being transported/delivered within a hospital setting. Although the exemplary embodiments are shown and described with respect to various departments within a hospital, it will be understood by those of skill in the art that the system and method of the present invention may be used in a variety of different industries/facilities where it is desired to transport items between locations effectively and efficiently.

In one example, a pharmacy department may desire to send out a pharmaceutical item 108 to, for example, the emergency department of the hospital. A first user may scan the identification element 106 (e.g., barcode) on that pharmaceutical item 108. The pharmacy would normally maintain a record of that medication payload, the specific pharmaceutical which was/to be sent. The pneumatic tube system 100 may add optical sighting data that may include, among other things, a time stamp—for instance, of what time the item 108 leaves the pharmacy station, what time it arrives in the emergency department station, etc. As an option, a second user at the receiving the emergency department may also scan the item 108 (the pharmaceutical) and the carrier which would then establish a closed loop audit trail. That is valuable, for instance, where the payload item were a narcotic which will now have an identifiable chain of custody.

In many institutional settings of even moderate size, such as hospitals, most of the items transported through a pneumatic tube system already have a barcode on them. In other words, sensitive items like pharmaceuticals tend to be barcoded or otherwise labeled with product information. Almost all lab specimens are barcoded. System users like hospital institutions use barcode technology heavily to keep track of delivered payload items. Indicia like barcodes prove quite useful.

Using the pharmacy example for further illustration, much as the pharmacy department scans a barcode on a pharmaceutical, the information reader 104 would effectively read that barcode based on database information established for the system 100. The system 100 could then assign different characteristics to this upcoming transaction based on what the specific payload item 108 is. For example, if the payload item 108 is in fact a narcotic or other such controlled substance, a pharmacy technician would scan the pharmacy item's barcode at the pneumatic tube station, the PTS control module 110 would then analyze the identifying information contained within the barcode including the data portion(s) indicating that the payload is a narcotic. Depending on the particular needs or desires of the hospital institution employing the system, such payloads will be identified as a high priority transaction. The software executed by the system controller would then carry out appropriate responsive action, such as placing the delivery transaction for this payload at 'the front of the line,' to get priority handling/treatment in the system.

Practical reasons may include, for example, the need to ensure that for such narcotic transport, the nurse on call at the receiving department is timely alerted to expect the incoming item. The system controller would initiate or prompt a signal sent out to the institution's nurse call system, so that the nurse on call (on duty) is alerted accordingly, and gives prompt attention to vigilantly await narcotic that is coming. Certain other criteria may be attached to that pharmaceutical based on its barcode read.

There are other actions that may be executed depending on the requirements of the particularly intended application. For example, when a barcode is read, the PTS control module 110 may be configured to flag as much in the system. In a typically implemented system, there is an engineering control panel. The engineering control software executed for that panel in a hospital is used by the hospital's engineering personnel to monitor the pneumatic tube delivery system. Based on the reading of a specific item's barcode the system may flag a transaction so that the monitoring engineer/maintenance technician would know that a specific transaction has a very high priority value item in it. Therefore, if for some reason the transaction triggers an alarm, or does not deliver successfully, that individual knows to jump into or otherwise take immediate remedial action. There are numerous other ways depending on the given institutions' and users' needs to link a delivery transaction payload's barcode read, and treat the delivery transaction differently responsive to certain information captured from that barcode read.

The system 100 operates, therefore, to carry out suitable traffic management and routing functions in software. Preferably, the PTS control module 110 is programmably configured in software, executing to optimize the various transport/delivery traffic that it controls. The PTS control module 110 will, for example, determine available routes, determine the most efficient route, and then would determine when a carrier can leave an origin station. That is, the system determines when a route has become available. In certain embodiments, the system may be configured to go beyond merely establishing that anything sent from a particular station is of high priority. The disclosed system more adaptively and dynamically determines appropriate priority levels on an item-by-item, or transaction-by-transaction basis. Hence, an adaptive prioritization (as opposed to a fixed priority structure) is realized by the disclosed system.

Certain other measures may be employed so as to adaptively prioritize transactions/payload items, other than through the barcode reading approach illustrated. Although barcodes are already quite prevalent in use, information may be acquired using cooperative measures like a station-equipped reader and readable payload item ID tags, or using non-cooperative measures like optical scanning of various information carrying vehicles to identify a specific payload item. Suitable acquisition measures may also be employed which require no particular preparation of the item, like image processing of captured image, processing of other parametric data (for example, size, weight, texture, . . . ) captured for/of the payload item using one or more sensors and its attendant delivery priority or need for special handling.

Continuing with an applicational example, the payload item in question may be a blood specimen sent from a baby. The sample is typically very hard to pull, and babies don't have a lot of blood, so that sample would be particularly valuable. It should not be lost or delayed in transport through the system. Once the blood specimen is taken from the baby, a barcode would be placed on its containment vial, tube, or the like. The system would recognize baby's blood as such and determine that it is a high priority payload item. The system would then take steps to ensure it is at or near the top of the line for delivery, while accordingly alerting the receiving station that it's on the way.

The information, data, and knowledge on which prioritization is determined may be predetermined based on the particular needs, requirements, and/or resources available at the given hospital or other facility/institution. Preferably, a database is established and suitably maintained, which knowledgeable and authorized hospital personnel would be able to access through a suitable user interface to set up and update these types of priorities. Examples of priorities established in the database may include an indication as to whether a payload is a blood product, a controlled substance, a highly perishable item, and so forth. As another example, the hospital staff may establish a quantitative scale (such as a scale of 1 to 5) where a level 1 might represent a run of the mill transaction of minimal handling priority (such as an empty carrier for maintenance), a level 2 may represent a common non-sensitive item such as Tylenol or aspirin, urine specimens, or the like. Levels 3, 4, and 5 may represent transactions of progressively higher sensitivity. For example, levels 3 and 4 may represent transactions for different types of blood products (urgency depending on time out of refrigeration, for instance, as all blood products have a limited permissible time out of refrigeration) while level 4 may include narcotics and other controlled and/or highly addictive or lethal substances. Level 5 may then be reserved for other even more time-critical transactions like highly perishable specimens taken from young children, a spinal tap for analysis, or the like.

In operation, the system 100 scans an item's barcode and reads the same to the extent it can classify the item 108 according to the given priority levels. Based on the classification, the PTS control module 110 automatically carries out the prescribed priority level-appropriate execution for the transaction, including automatic initiation of other non-transport related actions like alerting the receiving station through other system infrastructures if necessary.

Preferably, procedures (or even a default priority level) are in place for items not having a barcode or other indicia to read in this regard. System handling of such item transactions would follow accordingly.

For maximum flexibility, the database118 supporting such transaction based adaptive prioritization may, in certain embodiments, be updated by facility personnel serving various functions. In a hospital context, a triage nurse may be given the ability to set a priority level (perhaps even overriding the level automatically set) for a certain transaction. Similarly, a user interface or station may be provided where personnel such as a pharmacy technician may manually type in or push a button to assign a higher priority level for an item, making it a level 5 for instance in the preceding example. Care must be taken in such embodiments to prevent abuse and subsequent dilution of priority levels. For example, such prioritizing access may be limited to specific employees for that reason.

The system controller preferably includes a management interface where the given institution's leadership may set their own business/operational processes and pre-identify their priorities. In particular, managerial users may update and/or set transport characteristics and priorities to be associated with specific types of items 108 and transactions via the user interface 120. This provides not only a transactional priority system, it may also determine what other collateral actions (like alerts, flagging, . . . ) may be appropriate in connection with the various item delivery transactions. For example, with certain delivery transactions, the system may be specifically configured to initiate an automatic email, make a phone call, synchronously activate a light in a hallway, sound an alarm at the sending and/or receiving station, or otherwise trigger various other responsive events based on the characteristics preselected and attached to specific items automatically identified based on the barcode/indicia thereof. These priorities and other the transport characteristics may be stored in, for example, the Transport Characteristics Database 118.

A primary function of the system 100 would include optimizing delivery transaction scheduling and routing. If an urgent transaction were not prioritized, it would take its place in the queue behind other earlier-scheduled transactions. It is not uncommon even in modestly sized institutions for such transactions to wait on the order of 5 minutes leaving the sending station. By adaptive prioritization as disclosed herein, the system may immediately recognize a transaction's urgency and appropriately upgrade its place in the queue. If the priority level were determined to be high enough for this transaction's payload, it may be bumped instantly up to the #1 spot in rank for prompt delivery.

Depending on an institution's particular needs, multiple databases (primary and secondary, for instance) may be set up to establish a multi-level prioritization scheme. For example, hospitals may have a problem with people becoming addicted to pain medications. The problem may even preclude handling of controlled products like narcotics by certain hospital staff, such as those who typically work long hours and for that reason may be particularly vulnerable or fallible in this regard. Also, it is not uncommon to have a nurse or other staff member restricted from handling such items due to a past drug conviction or the like. The system may be programmed so that upon reading the item's barcode from the pharmacy and recognizing its destination to be a nursing station under such handling restriction, it causes the item's carrier upon arrival at the receiving station to be hold above the pneumatic tube station until retrieved by properly authorized personnel. For example, system may hold the carrier securely above an access port and only drop it into the access port or bin when it may be retrieved after that nurse has scanned his/her badge to identifying him/herself as an authorized recipient of the delivery. The system may query an employee database upon the nurse's entry of badge information to determine whether that employee is able to accept, then grant or deny access at the receiving station accordingly.

This type of access control may also be customized further. In certain cases, for instance, a certain nurse may be precluded from ever accessing narcotics or, the database may be configured to permit her access only under certain delineated conditions. In still other cases, this nurse may be given access to certain medications, but not others. Operational controls such as this may be quite specifically configured in the database to suit any given institution's unique business rules and requirements for a particular application.

Transactions may also be selectively adjusted in certain instances. Where a transaction of one priority has been awaiting delivery for longer than a pre-set time, for example, it may be bumped up in priority over certain others even if some of those others have a higher priority. Preferably, as transactions age, assuming everything else to be equal, the aging transaction's priority is elevated automatically accordingly. As an example, an ageing transaction may be multiplied by an increasing factor in priority with each additional minute it idles awaiting delivery.

Those skilled in the art will understand that the above-described exemplary embodiments may be implemented in any number of manner, including as a separate software module, as a combination of hardware and software, etc. For example, the PTS control module 110 may be programs containing lines of code that, when compiled, may be executed on a processor.

Although this invention has been described in connection with specific forms and embodiments thereof, it will be appreciated that various modifications other than those discussed above may be resorted to without departing from the spirit or scope of the invention as defined in the appended claims. For example, equivalent elements may be substituted for those specifically shown and described, certain features may be used independently of other features, and in certain cases, particular applications of elements may be reversed or interposed, all without departing from the spirit or scope of the invention.

What is claimed is:

1. A method for transporting items via a pneumatic delivery system including a network of conduits, comprising:
   identifying an item to be transported via the pneumatic delivery system by acquiring identifying information from an identifying element applied to the item;
   determining an item-specific transport characteristic of the item based on the acquired identifying information;
   determining a priority level for a pneumatic transport of the item through the network of conduits based on the acquired identifying information; and
   setting parameters for the pneumatic transport of the item through the network of conduits based on the transport characteristic of the item and the priority level.

2. The method of claim 1, wherein the identifying element is one of an RFID tag, a barcode, a QRC code, and an image indicia.

3. The method of claim 1, wherein the item-specific transport characteristic includes one of a preferred routing, an alert, access permissions, location restrictions, time of day restrictions, control software graphical user interface messages and error handling preferences.

4. The method of claim 1, wherein determining the transport characteristic of the item includes mapping the acquired identifying information to transport characteristics stored in a transport characteristics database.

5. The method of claim 1, wherein a destination address for the item to be transported is determined based on the acquired identifying information.

6. The method of claim 1, wherein setting the parameters includes one of indicating a level of priority and indicating a preferred route of the pneumatic transport of the item.

7. The method of claim 1, further comprising sending an alert to users based on the determined transport characteristic.

8. The method of claim 1, further comprising tracking a position of the item within the pneumatic delivery system.

9. The method of claim 1, further comprising storing user-specified transport characteristics within a transport characteristics database.

10. The method of claim 1, wherein the item to be transported is one of a pharmaceutical, a blood product and a lab specimen.

11. A system for transporting items, comprising:
an identifying element affixed to an item to be transported between stations of a network of delivery conduits, the identifying element including identifying information regarding the item;
an identification reader acquiring the identifying information from the identifying element; and
a processor analyzing the identifying information to determine an item-specific transport characteristic of the item based on the acquired identifying information and to determine a priority level for a pneumatic transport of the item through the network of delivery conduits based on the acquired identifying information, the processor further setting parameters for the pneumatic transport of the item through the network of delivery conduits based on the transport characteristic of the item and the priority level.

12. The system of claim 11, wherein the identifying element is one of an RFID tag, a barcode, a QRC code, and an image indicia.

13. The system of claim 11, wherein the identification reader is one of a barcode reader and an RFID scanner.

14. The system of claim 11, wherein the item-specific transport characteristic includes one of a preferred routing, an alert, access permissions, location restrictions, time of day restrictions, control software graphical user interface messages and error handling preferences.

15. The system of claim 11, wherein the processor determines the transport characteristic of the item by mapping the acquired identifying information to transport characteristics stored in a transport characteristics database.

16. The system of claim 11, wherein the processor determines a destination address of the item to be transported based on the acquired identifying information.

17. The system of claim 11, wherein the processor sets the parameters by one of indicating a level of priority and indicating a preferred route of the pneumatic transport of the item.

18. The system of claim 11, wherein the processor sends an alert to users based on the determined transport characteristic.

19. The system of claim 11, further comprising a plurality of sensors located within the network of delivery conduits for tracking a position of the item therewithin.

20. The system of claim 11, further comprising a memory storing user-specified transport characteristics.

21. The system of claim 11, wherein the item to be transported is one of a pharmaceutical, a blood product and a lab specimen.

22. A pneumatic delivery system, comprising:
a network of delivery conduits extending between a plurality of sending stations and receiving stations;
an identifying element affixed to an item to be transported between one of the sending stations and one of the receiving stations, the identifying element including identifying information regarding the item;
an identification reader acquiring the identifying information from the identifying element; and
a processor analyzing the identifying information to determine an item-specific transport characteristic of the item based on the acquired identifying information and to determine a priority level for a pneumatic transport of the item through the network of delivery conduits based on the acquired identifying information, the processor further setting parameters for the pneumatic transport of the item through the network of delivery conduits based on the transport characteristic of the item and the priority level.

23. A non-transitory computer readable storage medium including a set of instructions executable by a processor, the set of instructions, when executed by the processor, causing the processor to perform operations, comprising:
identifying an item to be transported via a pneumatic delivery system including a network of delivery conduits by acquiring identifying information from an identifying element applied to the item;
determining an item-specific transport characteristic of the item based on the acquired identifying information;
determining a priority level for a pneumatic transport of the item through the network of delivery conduits based on the acquired identifying information; and
setting parameters for the pneumatic transport of the item through the network of delivery conduits based on the transport characteristic of the item and the priority level.

* * * * *